United States Patent [19]

Inoue et al.

[11] Patent Number: 4,904,597
[45] Date of Patent: Feb. 27, 1990

[54] METHOD FOR CULTIVATION OF BACTERIA OF THE GENUS CAMPYLOBACTER

[75] Inventors: Yoshiaki Inoue; Jun Hoshino, both of Tokyo, Japan

[73] Assignee: Mitsubishi Gas Chemical Company, Inc., Tokyo, Japan

[21] Appl. No.: 922,711

[22] Filed: Oct. 24, 1986

[30] Foreign Application Priority Data

Oct. 29, 1985 [JP] Japan .................... 60-240483

[51] Int. Cl.⁴ ................ C12M 1/00; C12M 1/04; C12N 1/00
[52] U.S. Cl. .................. 435/252.1; 435/287; 435/313; 435/243
[58] Field of Search .............. 435/253, 287, 313, 243, 435/801; 252/373

[56] References Cited

FOREIGN PATENT DOCUMENTS 82111137 9/1971 European Pat. Off. .
0081202 11/1972 European Pat. Off. .
86402398 8/1978 European Pat. Off. .
709215 11/1972 France .
2083496 3/1971 United Kingdom .

Primary Examiner—Thomas G. Wiseman
Assistant Examiner—Patricia Carson
Attorney, Agent, or Firm—Ladas & Parry

[57] ABSTRACT

Disclosed is a simple method for cultivation of bacteria of the genus Campylobacter with good growth of bacteria which comprises carrying out the cultivation in a sealed container of gas barrier type in which are enclosed a medium inoculated with bacteria and a carbon-dioxide-generating type oxygen-removing composition packed in a gas permeable packaging material, oxygen concentration and carbon dioxide concentration in the container being adjusted to 0.5–15% and 0.5–22%, respectively within 5 hours from the initiation of the cultivation and these concentrations being kept for at most 72 hours.

4 Claims, No Drawings

METHOD FOR CULTIVATION OF BACTERIA OF THE GENUS CAMPYLOBACTER

BACKGROUND OF THE INVENTION

This invention relates to a method for cultivation of bacteria of the genus Campylobacter and more particularly it relates to a method for cultivation of bacteria of the genus Campylobacter which are causative of diarrhoea and are detected in a high percentage of diarrhoea patients and thus are widely attracting attention in the field of public health.

The bacteria of the genus Campylobacter are gram-negative and microaerophilic bacteria which are represented by *Campylobacter jejuni, Campylobacter coli,* etc. and do not grow under aerobic conditions and also hardly grow in ordinary anaerobic culture and require oxygen in an amount of 3–15% for growth. In Japan, percentage of detection of bacteria of the genus Campylobacter from diarrhoea patients is 9–16% for infants and 3–8% for adults. Thus, now they are widely attracting attention as causative bacteria for diarrhoea and they are cultivated for confirming the causes for diarrhoea.

However, bacteria of the genus Campylobacter are required to cultivate in a specially prepared gaseous atmosphere because they are microaerophilic bacteria and hitherto the following culturing methods have been known.

(1) Method Which Uses a Mixed Gas

According to this method, cultivation is carried out in an anaerobic jar equipped with a pressure gage and a gas-enclosing stopper in which a plate or a tube having a medium inoculated with a bacterium of the genus Campylobacter is placed and in which a mixed gas comprising 5% of oxygen, 10% of carbon dioxide and 85% of nitrogen is enclosed. This method is disclosed in "Medical Technology" 10, 219 (1982).

(2) Method Which Uses a Gas Generating Bag

This method uses Anaerocult C commercially available from Merck & Co., Inc. That is, according to this method, cultivation is carried out in an anaerobic jar in which are enclosed a Petri dish having a medium inoculated with a bacterium and a gas-generating bag in which water is poured just before it is enclosed in the jar to adjust $CO_2$ and $O_2$ concentrations in the system to 6–9% and 6–9% after 3 hours and finally 8–10% and 5–7%, respectively.

(3) Carbon Dioxide Cultivation Method

This method relates to the candle jar method disclosed in "Medical Technology" 10, 219 (1982). Growth of bacteria of the genus Campylobacter is very poor in the presence of 15% or more of oxygen even if carbon dioxide is present. According to this method, however, growth is accelerated by increasing resistance against oxygen to some extent with use of special media.

The conventional methods for cultivation of bacteria of the Campylobacter have the following defects.

That is, (1) the method which uses a mixed gas requires a special device for enclosing a mixed gas of oxygen, carbon dioxide and nitrogen and besides the operating is complex. Furthermore, since an anaerobic jar is used, progress of growth cannot be observed from the outside. (2) The method using a gas-generating bag requires an operation for pouring water in the bag and the gas concentrations in the system may vary with changes of amount of water added. Since an anaerobic jar is used, progress of growth cannot be observed from the outside. (3) In the case of the carbon dioxide cultivation method, a special medium is needed and besides growth of bacteria is not satisfactory.

The inventors have made an intensive research in an attempt to remove these problems, namely, to attain satisfactory growth of bacteria by a simple method and as a result this invention has been completed.

SUMMARY OF THE INVENTION

This invention provides a method for cultivation of bacteria of the genus Campylobacter, characterized in that the cultivation is carried out in a sealed container in which are enclosed a medium inoculated with a bacterium and a carbon dioxide-generating type oxygen remover at an oxygen concentration of 0.5–15% and a carbon dioxide concentration of 0.5–22% in the container.

DESCRIPTION OF THE INVENTION

The method for cultivation of this invention is performed by placing in a sealed container a carbon dioxide-generating type oxygen remover capable of adjusting in a short time the gaseous atmosphere to an oxygen concentration and a carbon dioxide concentration at which bacteria can grow most rapidly and a medium inoculated with a bacterium of the genus Campylobacter.

That is, according to the method of this invention, a medium inoculated with bacteria of the genus Campylobacter and a carbon dioxide-generating type oxygen remover are enclosed in a sealed container whereby the concentration of oxygen and that of carbon dioxide are adjusted to 0.5–15% and 0.5–22%, respectively within 5 hours, preferably 3–8% and 13–18%, respectively within 3 hours and these concentrations are maintained. Thus, growth of the bacterium of the genus Campylobacter is accelerated.

The carbon dioxide-generating type oxygen remover used in the present cultivation method comprises a composition which has an action of rapid absorption of oxygen and generation of carbon dioxide and which is packed in a gas permeable packaging material.

Examples of such compositions are as follows:

(1) Compositions which comprise a dithionite—a hydrogencarbonate—a carbonate—water. (See Japanese Patent Examined Publication No. 19729/72 and U.S. Pat. No. 4,102,803.)

(2) Compositions which comprise a reducing organic substance—a hydrogencarbonate—water.

As the reducing organic substance, there may be used, for example, catechol, ascorbic acid and/or salts thereof, erythorbic acid and/or salts thereof and the like. (See U.S. Pat. No. 4,337,276.)

(3) Compositions which comprise an oxygen-removing agent mainly composed of iron—a hydrogencarbonate—an acidic substance—water. (See Japanese Patent Unexamined Publication No. 150433/81.)

Any of the carbon dioxide-generating type oxygen removers having these materials packed therein may be used as long as when they are enclosed in a sealed container together with a medium inoculated with a bacterium of the genus Campylobacter, they can adjust the gaseous atmosphere in the container to an oxygen concentration of 0.5-15% and a carbon dioxide concentration of 0.5-22% within 5 hours by absorbing oxygen in the container and generating carbon dioxide. However, those which are principally composed of dithionite are preferred because of easiness in adjustment of oxygen absorbing rate and carbon dioxide-generating rate and especially preferred are compositions comprising a dithionite—a hydrogencarbonate—an aqueous electrolyte solution—a carrier material for the aqueous electrolyte solution or a dithionite—a hydrogencarbonate—a carbonate—an aqueous electrolyte solution—a carrier material for the aqueous electrolyte solution.

The oxygen removers containing a dithionite comprises generally 0.025-0.5 g of a dithionite, 0.05-7 g of a hydrogencarbonate, 0.002-0.2 g of an aqueous electrolyte solution and 0.01-4 g of a carrier for the aqueous electrolyte solution, preferably 0.06-0.2 g of a dithionite, 0.3-3.5 g of a hydrogencarbonate, 0.005-0.1 g of an aqueous electrolyte solution and 0.03-2 g of a carrier for the aqueous electrolyte solution for 100 ml of air in the closed system containing the medium together with the oxygen remover. When said composition contains a carbonate, the addition amount of the carbonate is 0.001-0.6 g, preferably 0.006-0.1 g each 100 ml of air in the closed system. These amounts are in proportion to the amount of air in the closed system and, for example, when the amount of air is 2 l, they are used in the amounts 20 times the above mentioned amounts.

The dithionites used in this invention absorb oxygen in coexistence with water with generating carbon dioxide upon reaction with a hydrogencarbonate or a carbonate and they may be used as Na salt, Zn salt, K salt, etc. preferably as Na salt.

The carbonates are added for adjustment of the ratio of carbon dioxide/oxygen and for prevention of reduction in performance of the oxygen remover. As examples, mention may be made of Na salt, Ca salt, K salt, Ba salt, $NH_4$ salt, etc., among which Na salt and Ca salt are preferred.

The hydrogencarbonates react with the dithionite which has absorbed oxygen, thereby to produce carbon dioxide. Examples thereof are Na salt, Ca salt, K salt and the like and preferred is the Na salt.

The aqueous electrolyte solution acts on the dithionite to accelerate absorption of oxygen and generation of carbon dioxide. Any electrolytes may be used as long as they are soluble in water and usually there may be used sulfates, carbonates, nitrates, halides, hydroxides, etc. and preferred are halides, more preferred are NaCl and $CaCl_2$. Concentration of the aqueous electrolyte solution is 0.01-60%, preferably 1-40%.

The carrier materials for the aqueous electrolyte solution stabilize the absorption of oxygen and generation of carbon dioxide and prevent decomposition of dithionite by their uniform supply of the aqueous solution to dithionite and they are in the form of powder or particle and can be well impregnated with the aqueous solution. For example, zeolite, activated charcoal, silica gel, etc. may be used and activated charcoal is the most preferred.

As materials for packing these compositions, there may be used any of those through which oxygen and carbon dioxide can well permeate, but preferred are those which have an oxygen permeability and a carbon dioxide permeability of at least 300 ml/Hr.$m^2$. atm, more preferably at least 1000 ml/Hr.$m^2$. atm. As examples of these packaging materials, mention may be made of non-woven fabrics, papers, microporous films and composites of these materials.

As the containers for enclosing a medium inoculated with a bactrium of the genus Campylobacter together with a carbon dioxide-generating type oxygen remover, there may be used any of those which have such air tightness as can maintain oxygen concentration and carbon dioxide concentration in the system at 0.5-15% and 0.5-22%, respectively. Generally, an anaerobic jar or bag may be used and the bag, especially the transparent plastic bag, is preferred for the method of this invention because the state of culture can be observed from the outside, amount of air can be simply and easily specified, it can be burnt up after use and no expensive devices are required. The bag may be made of nylon, PET, PE, PP, polyvinyl chloride, vinylon, etc. having an oxygen permeability of 100 ml/$m^2$. day.atm or less, more preferably 50 ml/$m^2$. day.atm or less, each alone or as composite thereof.

When the bag is sealed after the medium and the oxygen remover have been placed therein, the sealing is performed by heat sealing the edge portions of films or sheets to form a bag or heat sealing the open edge of a bag or sealing the open edge by a sealing bar.

The media used for the method of this invention comprise components generally used for cultivation of bacteria of the genus Campylobacter and include solid media such as agar media in a container such as Petri dish, liquid media in a tupe, etc. When a medium inoculated with a bacterium of the genus Campylobacter is enclosed in a sealed container together with a carbon dioxide-generating type oxygen remover according to this invention, the medium is usually placed in a Petri dish or a tube. In this case, the medium and the oxygen remover are placed so that they do not contact with each other.

Thus, bacteria of the genus Campylobacter can be cultivated by enclosing in a container of gas barrier type a medium inoculated with a bacterium of the genus Campylobacter and a carbon dioxide-generating type oxygen remover, sealing the container and carrying out cultivation at 37° C.–43° C. for 48-72 hours.

As explained above, the method for cultivation of bacteria of the genus Campylobacter according to this invention has the following effects.

(1) No special devices are required.
(2) Oxygen and carbon dioxide concentrations can be adjusted to those optimum for growth of bacteria.
(3) Many test bodies can be dealt with.
(4) The cultivation can be easily performed with simple materials.
(5) When cultivation is carried out using a bag, progress of growth of bacteria can be observed from the outside.

EXAMPLES 1-6

A small quantity of strains of *Campylobacter jenuni* previously isolated and subcultured on a blood agar medium were inoculated in a blood broth in a tube. This tube was placed in an anaerobic jar J-10 (manufactured by Hirayama Seisakusho Co.) and the gaseous atmosphere in the jar was replaced with a mixed gas composed of 5% of oxygen, 10% of carbon dioxide and 85% of nitrogen. After cultivation in this jar at 37° C. for 48 hours, 0.1 ml of the medium was spread on a blood agar plate medium or a Butzler's blood agar plate medium. A Petri dish of 98 mm in diameter and 16 mm in depth was used for placing the agar medium therein. (The Butzler's blood agar medium used herein comprises 1 l of a blood agar medium and 25,000 units of bacitracin, 50 mg of cycloheximide, 10,000 units of colistin sulphate, 15 mg of sodium cephazolin and 5 mg of novobiocin.) Thus, an agar plate medium inoculated with *Campylobacter jenuni* was prepared.

A carbon dioxide-generating type oxygen remover was prepared in the following manner. That is, a non-woven fabric Tyvec (manufactured by E. I. du Pont de Nemours & Co.) having an oxygen permeability of 10,000 ml/Hr.m$^2$.atm or a laminate film of paper (basis weight 40 g/m$^2$)/porous polythylene film having an oxygen permeability of 300 ml/Hr.m$^2$.atm as a packaging material was folded in two, and with heat sealing the three edge portions other than the fold a carbon dioxide-generating type oxygen-removing composition as shown in Table 1 was packed therein to obtain a carbon dioxide-generating type oxygen remover (50×50 mm).

Then, two pairs of the Petri dishes having therein the above prepared medium inoculated with the bacterium and the above prepared carbon dioxide-generating type oxygen remover were placed in a bag (235×130 mm) made of KON/PE (polyvinylidene chloride coated polypropylene/polyethylene) having an oxygen permeability of 10–30 ml/day m$^2$.atm and an open edge of this bag was sealed by a sealing bar. Content of air in the bag was 270 ml. Cultivation was effected with this bag at 37° C. and changes of oxygen and carbon dioxide concentrations with time in the bag were measured.

After cultivation for 72 hours, the number and diameter of colonies formed were measured. The results are shown in Table 1.

COMPARATIVE EXAMPLE 1

In an anaerobic jar (manufactured by Merck & Co.) were placed five pairs of Petri dishes having therein an agar plate inoculated with *Campylobacter jununi* and prepared in the same manner as in Examples and a gas-generating bag Anaerocult C (manufactured by Merck & Co.) in which 6 ml of water was poured by a measuring pipette and the jar was closed. Cultivation was carried out in the same manner as in Examples and the same measurements as in Examples were conducted. The results are also shown in Table 1.

TABLE 1

| | Carbon dioxide generating type oxygen removing compositions | | | | | |
|---|---|---|---|---|---|---|
| | Sodium di-thionite (g) | Hydrogen-carbonate (g) | Carbonate (g) | Aqueous electrolyte solution (g) | Carier material (g) | Packing material for oxygen removing composition |
| Example 1 | 0.27 | NaHCO$_3$ 1.7 | Na$_2$CO$_3$ 0.06 | 7% aqueous CaCl$_2$ solution 0.06 | granulated charcoal 1.9 | Non-woven fabric (Tyvec) |
| Example 2 | 0.27 | NaHCO$_3$ 1.7 | Na$_2$CO$_3$ 0.06 | 7% aqueous CaCl$_2$ solution 0.06 | granular material zeolite 4.0 | Non-woven fabric (Tyvec) |
| Example 3 | 0.27 | NaHCO$_3$ 1.7 | Na$_2$CO$_3$ 0.06 | 7% aqueous CaCl$_2$ solution 0.06 | Granulated charcoal 1.9 | Non-woven fabric (Tyvec) |
| Example 4 | 0.10 | NaHCO$_3$ 1.7 | Na$_2$CO$_3$ 0.06 | 7% aqueous CaCl$_2$ solution 0.06 | Granulated charcoal 1.9 | Non-woven fabric (Tyvec) |
| Example 5 | 1.35 | NaHCO$_3$ 1.7 | Na$_2$CO$_3$ 0.06 | 7% aqueous CaCl$_2$ solution 0.006 | Granulated charcoal 1.9 | Paper/porous polyethylene |
| Example 6 | 0.27 | NaHCO$_3$ 0.2 | Na$_2$CO$_3$ 0.00 | 7% queous CaCl$_2$ solution 0.06 | Granulated charcoal 1.9 | Non-woven fabric (Tyvec) |
| Comparative Example 1 | — | — | — | — | — | — |

| | The number of colony and diameter of colony formed after cultivation for 72 hours | | | |
|---|---|---|---|---|
| | Blood agar medium | | Butzler's blood agar medium | |
| | The number of colony/plate | Ratio of diameter* of colony | The number of colony/plate | Ratio of diameter* of colony |
| Example 1 | 152 | 1.5 | 151 | 1.6 |
| Example 2 | 156 | 1.45 | 155 | 1.65 |
| Example 3 | 149 | 1.55 | 152 | 1.6 |
| Example 4 | 150 | 1.0 | 149 | 1.05 |
| Example 5 | 150 | 1.35 | 151 | 1.35 |
| Example 6 | 153 | 1.55 | 152 | 1.65 |
| Comparative Example 1 | 148 | 1.0 | 153 | 1.0 |

| | Change of gas concentrations with time | | | | | | | |
|---|---|---|---|---|---|---|---|---|
| | Change of oxygen concentration with time (%) | | | | Change of carbon dioxide concentration with time (%) | | | |
| | 3 hr | 5 hr | 24 hr | 72 hr | 3 hr | 5 hr | 24 hr | 72 hr |
| Example 1 | 7.1 | 6.8 | 5.8 | 4.0 | 13.0 | 14.8 | 14.9 | 15.3 |

TABLE 1-continued

| | | | | | | | | |
|---|---|---|---|---|---|---|---|---|
| Example 2 | 7.4 | 7.1 | 5.9 | 3.8 | 12.1 | 13.9 | 14.1 | 14.8 |
| Example 3 | 7.4 | 6.1 | 5.5 | 3.9 | 12.2 | 13.9 | 14.5 | 16.1 |
| Example 4 | 11.7 | 11.4 | 11.2 | 11.1 | 8.3 | 8.5 | 8.5 | 8.6 |
| Example 5 | 14.7 | 12.7 | 6.3 | 0.8 | 4.3 | 6.2 | 12.5 | 18.2 |
| Example 6 | 7.6 | 6.2 | 5.4 | 4.8 | 7.5 | 7.7 | 8.0 | 8.2 |
| Comparative Example 1 | 8.7 | 8.5 | 8.0 | 7.8 | 6.7 | 6.8 | 7.5 | 7.7 |

*The ratio of diameter of colony = $\dfrac{\text{Average value of diameter of colonies in each Example}}{\text{Average value of diameter of colonies in Comparative Example 1}}$

We claim:

1. A method for cultivation of a bacterium of the genus Campylobacter which comprises steps,
   (1) enclosing, in a container of a gas-barrier material which is a bag made of a film having an oxygen permeability of 100 ml/m$^2$.day.atm or less and an open edge of the bag that is heat sealed or sealed by a sealing bar, mediums inoculated with bacterium of the genus Campylobacter and packages of a gas-permeable material containing therein a material capable of generating carbon dioxide and absorbing oxygen in the container with carbon dioxide generated in situ, said material capable of generating carbon dioxide comprising 0.025–0.5 g of a dithionite, 0.05–7 g of a hydrogencarbonate, 0.001–0.6 g of a carbonate, 0.002–0.2 g of an aqueous electrolyte solution and 0.01–4 g of a carrier for the electrolyte, for every 100 ml of air present in the container, wherein the composition is packed in a packaging material having an oxygen permeability and a carbon dioxide permeability of at least 300 ml/Hr.m$^2$.atm,
   (2) beginning to cultivate the bacterium under such conditions that oxygen and carbon dioxide concentrations in the container are controlled to 3–8% and 13–18%, respectively, within 5 hours from initiation of the cultivation at 37°–43° C., and
   (3) keeping the oxygen and carbon dioxide concentrations in the container for at most 72 hours.

2. A method according to claim 1 wherein the hydrogencarbonate of the material is sodium hydrogencarbonate and the carbonate is sodium carbonate.

3. A kit used for cultivation of a bacterium of the genus Campylobacter which comprises, in a container of a gas-barrier material which is a bag made of a film having an oxygen permeability of 100 ml/m$^2$.day.atm or less and an open edge of the bag that is heat sealed or sealed by a sealing bar, vessels containing a medium inoculated with a bacterium of the genus Campylobacter and packages of a gas-permeable material containing therein a material capable of generating carbon dioxide and absorbing oxygen in the container with carbon dioxide generated in situ, said material capable of generating carbon dioxide comprising 0.025–0.5 g of a dithionite, 0.05–7 g of a hydrogencarbonate, 0.001–0.6 g of a carbonate, 0002–0.2 g of an aqueous electrolyte solution and 0.01–4 g of a carrier for the electrolyte, every 100 ml of air present in the container wherein the composition is packed in a packaging material having an oxygen permeability and a carbon dioxide permeability of at least 300 ml/Hr.m$^2$.atm.

4. A kit according to claim 3 wherein the hydrogencarbonate of the material is sodium hydrogencarbonate and the carbonate is sodium carbonate.

* * * * *